(12) United States Patent
Iddan et al.

(10) Patent No.: US 7,708,705 B2
(45) Date of Patent: May 4, 2010

(54) SYSTEM AND METHOD FOR SENSING IN-VIVO STRESS AND PRESSURE

(75) Inventors: Gavriel J. Iddan, Haifa (IL); Zvika Gilad, Haifa (IL)

(73) Assignee: Given Imaging Ltd., Yoqneam (IL)

( * ) Notice: Subject to any disclaimer, the term of this patent is extended or adjusted under 35 U.S.C. 154(b) by 166 days.

(21) Appl. No.: 10/519,918

(22) PCT Filed: Jul. 3, 2003

(86) PCT No.: PCT/IL03/00559

§ 371 (c)(1),
(2), (4) Date: Jan. 3, 2005

(87) PCT Pub. No.: WO2004/004540

PCT Pub. Date: Jan. 15, 2004

(65) Prior Publication Data

US 2005/0228308 A1 Oct. 13, 2005

Related U.S. Application Data (60) Provisional application No. 60/393,300, filed on Jul. 3, 2002, provisional application No. 60/435,363, filed on Dec. 23, 2002.

(51) Int. Cl.
*A61B 5/103* (2006.01)
*A61B 5/117* (2006.01)
(52) U.S. Cl. ..................................... 600/587; 600/561

(58) Field of Classification Search ................. 600/587, 600/593, 595, 101, 160
See application file for complete search history.

(56) References Cited

U.S. PATENT DOCUMENTS 3,939,823 A * 2/1976 Kaye et al. .................. 600/561
4,278,077 A 7/1981 Mizumoto
4,329,881 A 5/1982 Schloss (Continued)

FOREIGN PATENT DOCUMENTS

KR 2002/089669 11/2002

(Continued)

OTHER PUBLICATIONS

International Search Report of International Application PCT/IL03/00559, dated Dec. 11, 2003.
U.S. Appl. No. 60/429,562, filed Nov. 29, 2002, Iddan et al.

*Primary Examiner*—Max Hindenburg
*Assistant Examiner*—Jonathan M Foreman
(74) *Attorney, Agent, or Firm*—Pearl Cohen Zedek Latzer, LLP (57) ABSTRACT

A device (4440), system and method may sense and/or analyze in-vivo pressure or stress, and may in addition sense other data such as for example, image data. An in-vivo device (4440) may include a stress or pressure sensor (4443), and possibly an additional sensor, such as an image sensor, a pH sensor, etc. In one example the stress or pressure sensor (4443) is connected to a shell (4444) of the device.

12 Claims, 9 Drawing Sheets

U.S. PATENT DOCUMENTS

| | | | |
|---|---|---|---|
| 4,854,328 A | 8/1989 | Pollack | |
| 5,604,531 A | 2/1997 | Iddan et al. | |
| 5,993,378 A | 11/1999 | Lemelson | |
| 6,240,312 B1 | 5/2001 | Alfano et al. | |
| 6,419,626 B1* | 7/2002 | Yoon | 600/109 |
| 2001/0035902 A1 | 11/2001 | Iddan et al. | |
| 2001/0051766 A1 | 12/2001 | Gazdzinski | |
| 2002/0103417 A1 | 8/2002 | Gazdzinski | |
| 2002/0162399 A1* | 11/2002 | Esashi et al. | 73/715 |
| 2003/0065250 A1* | 4/2003 | Chiel et al. | 600/115 |
| 2003/0191430 A1* | 10/2003 | D'Andrea et al. | 604/66 |
| 2004/0106849 A1* | 6/2004 | Cho et al. | 600/101 |
| 2004/0171915 A1 | 9/2004 | Glukhovsky et al. | |

FOREIGN PATENT DOCUMENTS

| | | |
|---|---|---|
| WO | WO 98/29030 | 7/1998 |
| WO | WO 01/08548 | 2/2001 |
| WO | WO 01/50941 | 7/2001 |
| WO | WO 01/65995 | 9/2001 |

\* cited by examiner

SYSTEM AND METHOD FOR SENSING IN-VIVO STRESS AND PRESSURE

CROSS-REFERENCE TO RELATED APPLICATIONS

This application is a National Phase Application of PCT International Application No. PCT/IL2003/000559, International Filing Date Jul. 3, 2003, entitled "SYSTEM AND METHOD FOR SENSING IN-VIVO STRESS AND PRESSURE", which in turn claims priority from United States Patent Applications, 60/393,300, filed Jul. 3, 2002, and 60/435,363, filed Dec. 23, 2002, all of which are incorporated by reference herein in their entirety.

FIELD OF THE INVENTION

The present invention relates to the field of diagnostic in vivo devices, more specifically, to a system and method for sensing stress and/or pressure in vivo.

BACKGROUND OF THE INVENTION

In vivo press can be indicative of organ's function; for example, of endo luminal conditions. The pressure in blood vessels, intra cerebral pressure or intra-gastric pressure, for example, may be indicative of the activity in these body lumens or of prevailing conditions in these lumens. The gastrointestinal (GI) tract is a typically convoluted body lumen starting from the oral cavity and proceeding through the esophagus, stomach, duodenum and small intestine and ending at the rectum; it is a long tube that folds many times to fit inside the abdomen. The small intestine is connected to the large intestine, which begins with the cecum, a small saclike evagination, then continues through the ascending colon, transverse colon, descending colon and the sigmoid (S-shaped) colon to the rectum. Portions of the GI tract are separated by muscular valves, such as the esophageal gate, separating the esophagus from the stomach, the pylorus, separating the stomach from the small intestine and the ileocecal valve separating the cecum from the colon. Such gates may be considered "motility gates" in the sense that motility of matter moving through the GI system may differ before and after passing through such gates. Matter, such as food, is passively moved through the GI tract and pushed through the valves due to the muscle action of the GI tract wall, namely, peristalsis. Thus, motility in the GI tract is achieved via pressure exerted by the GI tract walls.

Some gastrointestinal conditions or diseases, for example constipation, GERD (gastroesophageal reflux disease) and IBS (irritable bowel syndrome), are thought to be related to intestinal motility and are some times referred to as functional diseases (either the muscles of the organs or the nerves that control the organs are not working normally, and, as a result, the organs do not function normally). Whereas some gastrointestinal diseases can be seen and diagnosed with the naked eye or by microscopic examination of biopsies gastrointestinal functional diseases typically cannot be seen with the naked eye or with the microscope. In some instances, the abnormal function can be demonstrated by tests, for example, gastric emptying studies or antro-duodenal motility studies. However, these tests often are complex, are not widely available, and do not reliably detect the functional abnormalities. Accordingly, functional gastrointestinal diseases are identified, to date, by default, namely, diseases involving the abnormal function of gastrointestinal organs in which abnormalities cannot be seen in the organs with either the naked eye or the microscope.

Endo-luminal pressure, e.g., gastric pressure, may be measured by pressure sensors carried on the end of endoscopes or catheters However, these methods may cause patient discomfort and are of limited scope (for example, these methods are not useful for sensing the entire GI tact). They also, by being interventionist in nature, may distort the normal behavior thus distorting the results. Gastric pressure has been known to be measured and the information transmitted from the body by an autonomous ingestible device including, for example, a diaphragm assembly, which includes a diaphragm and elements such as coils, capacitors and a transistor. This assembly, which may be housed in a plastic cap or in a rubber sack, is inserted into the GI tract such that vibration of the gastrointestinal environment (typically containing fluids) is sensed. These measurements and measurements of pressure sensors used in other methods may be useful for indicating the hydrostatic pressure in a body lumen. The hydrostatic pressure is exerted uniformly throughout the lumen, and as such, is easily influenced by events that are unrelated to the activity or condition of the lumen itself. For example, pressure sensed in the GI tract can be affected by breathing and heart activity.

There is therefore a need for an improved system and method for sawing in vivo environments for parameters such as pressure, which might be indicative of a body lumen activity and/or of its condition.

SUMMARY OF THE INVENTION

According to an embodiment of the invention there is provided a system and method for sensing in vivo pressure. The term pressure typically relates to the force acting across a unit area whereas the term stress typically refers to forces acting within a solid or other object as a result of deformation and external forces.

According to some embodiments of the invention the system and method may be used as a diagnostic tool for intra luminal motility; other uses are within the scope of the invention.

According to one embodiment of the invention there is provided a system which includes a stress-responsive element. According to another embodiment the system includes a stress-responsive element that is coupled to a sensor such as a capacitive deflection sensor, a pressure sensor or a strain gauge. According to some embodiments, the system is configured for occupying a body lumen while being in close enough proximity to a body lumen wall to be contacted by at least a portion of the wall when the wall is contracted.

In one embodiment the system may include a sensor that may be in communication with a processor, for processing output of the sensor, and optionally, with a transmitter, for transmitting, the sensor output to a receiver. The processor may also be external to the in-vivo device; such as in an external workstation. In one embodiment the in vivo location and or orientation of the stress-responsive element can be known and processed to output information relate to the stress and/or pressure at specific locations in vivo. Optionally, the system, according to one embodiment may include additional sensors, such as an image sensor or bio-sensors (e.g., analytical devices incorporating a biological material or a biomimic such as tissue, microorganisms, organelles, receptors, enzymes, antibodies, nucleic acids etc., or other devices or substances) for providing additional data (such as image data) together with the stress data. The sensed signals as relayed to an external recorder and/or processor and/or display system may in some cases be used to activate components in the in-vivo device, for example drug release components.

The system according to one embodiment can be used to measure motility in the GI tract. According to another embodiment the system can be used to follow the passage of a device in vivo and/or localize a device in vivo.

BRIEF DESCRIPTION OF THE DRAWINGS

The present invention will be understood and appreciated more fully from the following detailed description taken in conjunction with the appended drawings in which.

DETAILED DESCRIPTION OF THE INVENTION

In the following description, various aspects of the present invention will be described. For purposes of explanation, specific configurations and details are set forth in order to provide a thorough understanding of the present invention. However, it will also be apparent to one skilled in the art that the present invention may be practiced without the specific details presented herein. Furthermore, well-known features may be omitted or simplified in order not to obscure the present invention.

Figure 1:
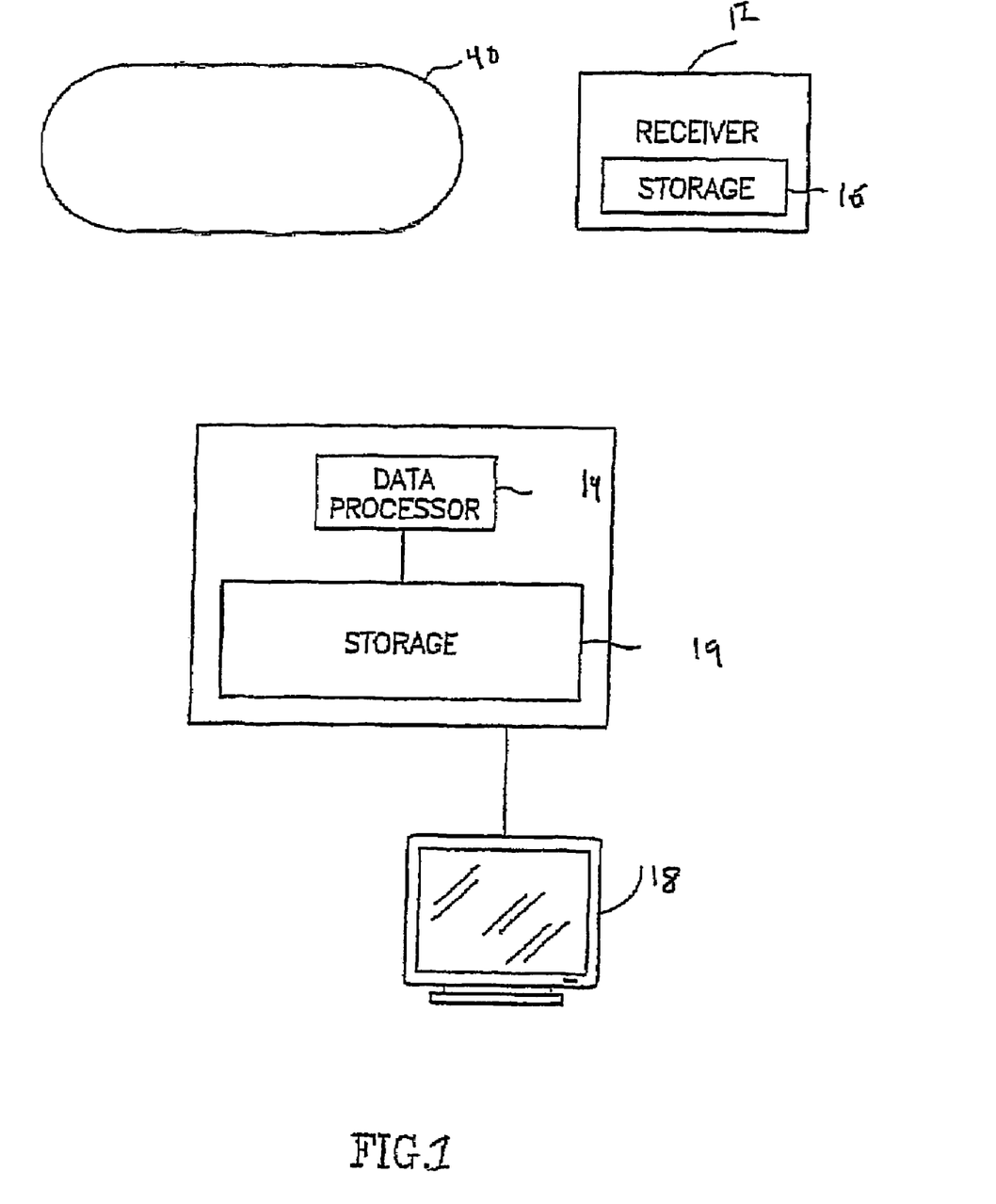
FIG. 1 depicts a diagnostic system according to an embodiment of the present invention.

Reference is now made to FIG. 1, in which a diagnostic system according to an embodiment of the present invention is depicted. Referring FIG. 1, typically, a device 40 transmits information to a receiver 12, typically located outside the patient's body in one or more locations. Receiver 12 typically includes an antenna or antenna array (not shown) usually but not necessarily, worn on a patient's body. The system also includes a data storage unit 16, a data processor 14, a data processor storage unit 19, and a monitor 18, for displaying, inter alia, stress or pressure data, image data, diagnostic data motility or location data, or other data, The data processor may be or include a receiver to receive data from receiver 12; alternately, receiver 12 may be included within or associated with data processor 14. When viewing the various data presented, the user is typically presented with one or more windows on monitor 18; in alternate embodiments windows need not be used. Typically, the receiver 12 and receiver storage unit 16 are small and portable, and are worn on the patient's body during recording of data, but may be of other configurations. Typically, data processor storage unit 19 includes a database 21 storing, for example, stress information, image information, or other information.

Typically, data processor 14, data processor storage unit 19 and monitor 18 are part of a personal computer or workstation, which includes standard components such as processor 14, a memory, a disk drive, and input-output devices, although alternate configurations are possible. Data processor 14 may include any standard data processor, such as a microprocessor, multiprocessor, accelerator board, or any other serial or parallel high performance data processor. Data processor 14 typically, as part of its functionality, acts as a controller controlling the display of data. Monitor 18 is typically a video display, but may, in addition, be any other device capable of displaying data.

In operation, the device 40 transmits information such as stress, strain, pressure, image or other data to receiver 12 using, for example, electromagnetic radio waves. Other transmission methods are possible, such as ultrasonic, infra-red, or other transmission methods. Typically, the device 40 is designed to contact the walls of the lumen being analyzed so as to, for example, measure the contractile forces of the muscle walls, or other forces, while directly contacting the walls.

Receiver 12 transfers the data to receiver storage unit 16. After a certain period of time of data collection, the data stored in storage unit 16 is sent to the data processor 14 or the data processor storage unit 19. For example, the receiver 12 or receiver storage unit 16 may be taken off the patient's body and connected to the personal computer or workstation which includes the data processor 14 and data processor storage unit 19 via a standard data link, e.g., a serial or parallel interface of known construction. An intermediate receiver and storage unit need not be used. The data is then transferred from the receiver storage unit 16 to a database 21 within data processor storage unit 19. Typically, the data is stored in the database 21, which may be implemented in a variety of known manners. In alternate embodiments the receiver 12 may be worn by the patient and at the same time be connected to data processor 14 for on-line communication and display.

Stress on the device 40 passing through the GI tract differs at different points in the GI tract, and may differ such that stress readings from the device 40 may be used to determine the position of the device or other information. For example, the device 40 may experience a certain stress when in the stomach a certain stress when passing through the pylorus, another stress when in the small intestine, etc. Further, the contractions of the GI tract was may be sensed by the device 40 and processed and analyzed by data processor 14.

Data processor 14 may analyze the data and provide the analyzed data to the monitor 18. If image data is collected still or moving images may be displayed on monitor 18, in addition to stress data. In one embodiment relatively rapid changes in stress may be used to determine that the device 40 has passed from one area of the GI tract to another, and thus the position status of the device 40 may be determined. For example, a series of stress changes may signify passage from the stomach, via the pylorus, to the small intestine, different stress intensities or different frequencies of events of stress can indicate different locations in the GI tract, and so on. Such data may be used to, for example, provide a motility analysis: the time the device 40 spends in each segment may be calculated and displayed on the monitor 18. Such data may be used to provide a device position, for example what section of the GI tract displayed images were taken from, which may be displayed on the monitor 18. The stress data itself may be provided to the data processor 14 and displayed on monitor 18, as a numerical value, as a graph (e.g., stress vs. time, or stress vs. distance traveled), in conjunction with image data, or in another format.

If image or other data is collected by the device 40, such data may be presented in conjunction with the stress data and/or data derived from the stress data. For example, an image or moving image may be displayed on monitor 18, and stress, location, motility or other data may be displayed which is relevant to the capture time of the currently displayed image or moving image sequence.

In an embodiment where image data is included, the image data recorded and transmitted by the device 40 may be, for example, digital color image data, although in alternate embodiments other image formats may be used. In an exemplary embodiment, each frame of image data includes 256 rows of 256 pixels each, each pixel including data for color and brightness, according to known methods. For example, in each pixel, color may be represented by a mosaic of four sub-pixels, each sub-pixel corresponding to primaries such as red, green, or blue (where one primary is represented twice). The brightness of the overall pixel is recorded by a one byte (e.g., 0-255) brightness value. Typically, images are stored sequentially in data processor storage unit 19. The stored data is included of one or more pixel properties, including color and brightness.

According to some embodiments, localization within a body lumen, such as the GI tract, can be performed, inter alia based on a detected stress, pressure or motility pattern. Stress, strain or pressure data can be transmitted from an in-vivo sensor and the transmitted data can be processed according to stress readings that are typical to different portions of the body lumen, thereby enabling localization of the sensor at least to a specific portion of the body lumen.

For example, an in-vivo device such as device 40 may measure contractile forces (e.g., corresponding to peristaltic pressure). Such measurements may be used, for example, by processor 14, to provide an indication of the location of the in-vivo device. For example, in the small intestine, periodic contractile forces may be recorded due to the peristaltic pressure, while in the stomach and colon such readings may differ, due to the less regular peristaltic pressure. As such a processor or analytical process can use such information to provide an indication of hen the device reaches the small intestine. In addition, different patterns of peristaltic pressure along the small intestine may provide an indication of the location of the device. Such indications may be, for example, displayed on monitor 18.

Figure 2:
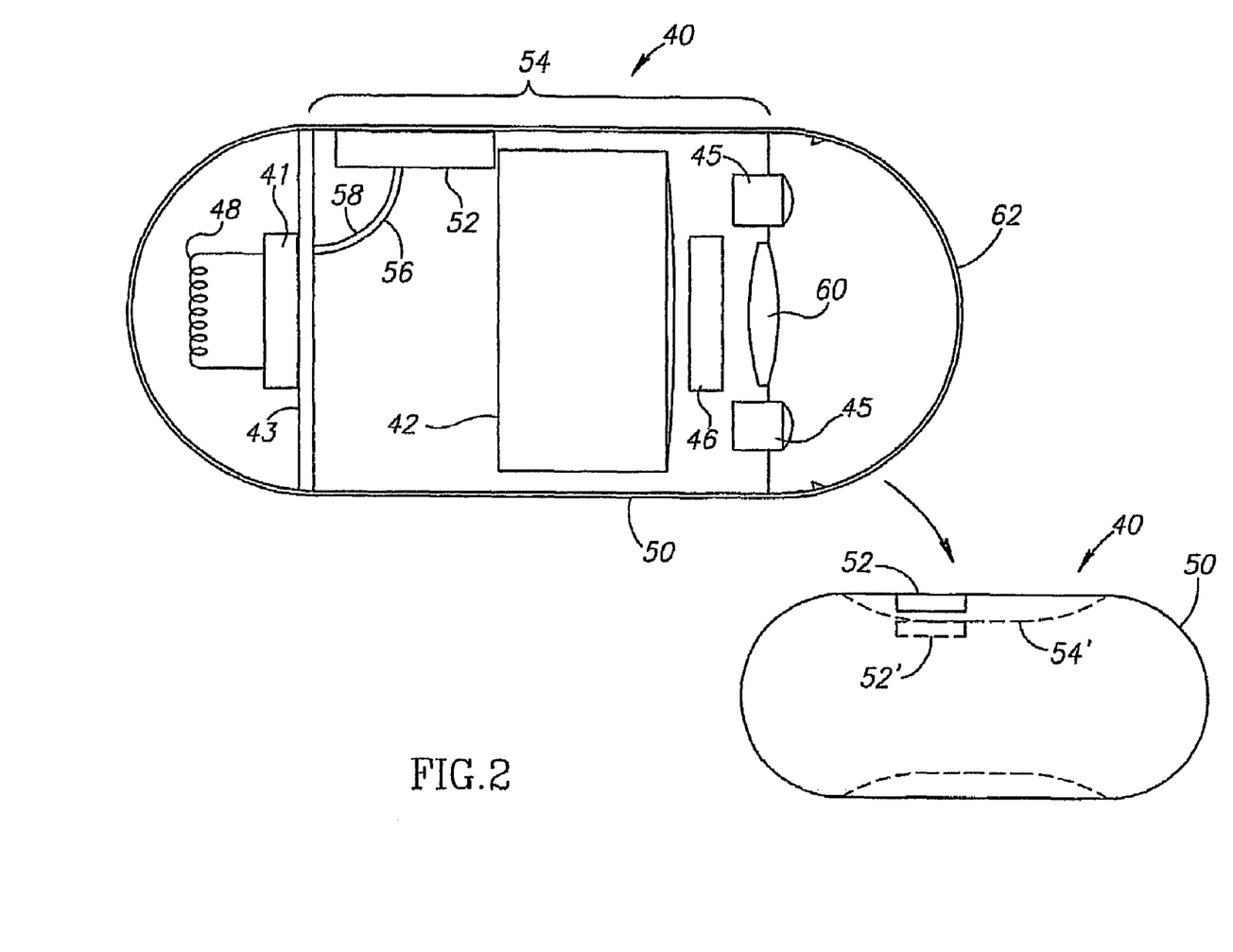
FIG. 2 is a schematic diagram of an in-vivo sensing device according to one embodiment of the present invention.

Reference is made to FIG. 2, which shows a schematic diagram of an in-vivo diagnostic system according to one embodiment of the present invention. In an exemplary embodiment, the system includes an ingestible device 40 including a container or shell 50 of about 0.2-0.8 mm, a strain gauge 52, a power source 42 such as a battery for powering the elements of the device 40, a circuit board 43, and a transmitter 41, for transmitting stress or pressure information and possibly other information to a receiving device and/or a processing device (e.g., receiver 12 and/or processor 14 of FIG. 1, although other receiver/display systems may be used). The transmitter 41 may transit via an antenna 48. Device 40, and other in-vivo devices shown herein, are typically in the form of an autonomous swallowable capsule, but may be in other forms; for example device 40 need not be swallowable or a capsule, and need not be autonomous.

Shell 50 typically includes a stress-responsive element or portion such as portion 54. Shell 50 typically forms at least part of the device—shell 50 may completely surround the device, but need not. Portion 54 or other stress or strain responsive element may respond to stress or strain by, for example, deforming, bending, moving, etc. Other embodiments may include differently shaped devices having shells of different thicknesses, and the shell 50 may be of variable thickness. Stress-responsive element or portion 54 may be or include other structures. For example, a stress-responsive element may include a piezo film such as, for example, PVDF (Polyvinylidene Fluoride), or a film including a strain gauge. For example, a stress-responsive element may be a separate piece attached to or connected to shell 50; for example a disk, sheet or other portion of semi rigid material which may deform in response to stress. In other embodiments additional sensors may be included. In other embodiments, a separate stress responsive portion need not be used; e.g., an entire shell or encapsulation may be stress responsive.

Power may be provided by methods other than a battery for example magnetic induction. Shell 50 and portion 54 may be shaped and configured so that when traveling through a lumen, the shell 50 and portion 54 are contacted by the lumen walls, and thus forces from the walls cause stress or strain on portion 54. The contact may be on more than one (or on all) sides of the shell 50, so as to ensure the forces from the walls are translated to the shell 50. For example, a capsule shaped shell 50 traveling through the GI tract may, in portions, be touched, on enough portions to be able to receive adequate forces. In alternate embodiment, full or partial contact with lumen walls is not required, and other shapes and configurations may be used.

The device 40 is swallowed by a patient and typically traverses the patients GI tract. Typically, the device and a receiving, recording, processing and display system that may be used with the device (e.g., as depicted in FIG. 1) are similar to and may contain elements similar to embodiments described in U.S. Pat. No. 5,604,531 to Iddan et al., and/or to embodiments described in published application WO01/65995 to Glukhovsky et al., both of which are assigned to the assignee of the present application, and both of which are incorporated herein by reference in their entirety. However, the device and a receiving, recording, processing and display system may have other structures and functionalities. In alternate embodiments the system may have different configurations and include other sets of components. For example, the system may include a needle shaped or other suitable shaped device for being inserted into blood vessels.

In one embodiment device 40 is sized and designed to occupy the small intestine while generally being in contact with the small intestine walls or while being in close proximity to the walls such that at least a potion of a wall will contact the device shell 50, in particular when the wall contract. The system according to other embodiments may be sized and shaped to occupy other body lumens while being in contact with a lumen wall or being in close enough proximity to the wall to be contacted by at least a portion of the wall when the wall is contracted.

Typically, the shell 50 is substantially semi-rigid, and may deform slightly under stress. In the inset in FIG. 2, portions of device 40 are deformed or are under stress due to external forces or pressure, for example stress exerted by the body lumen wall. For example, dotted lines 52' and 54' show an example of the position of portion 54 and strain gauge 52 after deformation. Deformation or stress need not result in visible movement. In other embodiments, stress may be from other than lumen walls, and a device need not be in contact with lumen walls to function.

In particular, in one embodiment deformation occurs in the portion 54, which may be the central portion of the shell 50, or a portion of the shell 50 near a pressure gauge. Deformation may occur in another region. Typically, the shell 50 includes polymer or plastic such as ISOPLAST™ (by Dow Chemicals); other suitable materials may be used. The strain gauge 52 may be incorporated in the shell or may be bonded to the shell 50; other methods of attachment or incorporation may be used. The strain gauge 52 may be, for example, a thin foil, for example a semiconductor, or a piezoelectric material. For example, PZT (piezoelectric zirconate titantes) or PVDF, or other suitable material, may be used. Such materials may, when compressed, emit an electric signal that is proportional to the amount of compression, or otherwise carry information on the amount of the compression. A sensor such as Endveco model 8507C may be used as the strain gauge, and may measure pressure in range of 2 to 50 pounds per square inch, with the full range output of 300 mv; other devices may be used. If required, the strain gauge 52 may accept power through wire 56 and may provide a variable strain signal on wire 58 to transmitter 41.

The device 40 is typically swallowed and moved through the GI tract by peristalsis. The contractions of the GI tract walls mall be sensed by the device 40 as stress exerted on the shell 50 (for example, in portion 54). The stress exerted by the GI tract walls may distort the shell 50. The gauge 52 is similarly distorted, or may be under stress, (e.g., as shown by the dotted line 52', although the skin gauge 52 may not actually deform) and produces a signal proportional to the strain experienced, and thus to the stress experienced by the device 40. The signal may be propagated on wire 58 to transmitter 41, to be transmitted to an external receiving device.

In an alternate embodiment the strain gauge 52 may be an integral part of the shell 50, for example, the entire shell 50 or parts of the shell (such as portion 54) may be made of piezo-electric material and may respond to stress by deforming. The deformation may result in an electric signal, such as the signal produced by a strain gauge. In this embodiment wires 56 and 58 may be connected to the shell 50.

Transmitter 41 may include or be part of a processor that processes stress data or other data. The transmitter 41 may include, for example, a one time programming unit (not shown), a control logic block (not shown), and other circuitry. The transmitter 41 may be an ultra low power radio frequency (RF) a with high bandwidth input, possibly provided in chip scale packaging. In alternate embodiments a separate processor may be used, within device 40 or in a unit external to the body; for example, processor 14 may be used. Transmitter 41 may include control capability for the device 40; alternately, a separate controller may be used.

If an imaging capability is desired, device 40 may include imaging components such as, for example, an imager 46 and a set of illumination elements 49 such as, for example, a set of white LEDs (other elements may be used) to illuminate an area for viewing. An optical dome 62 may provide a generally transparent cover for the optical elements, provides a sealed barrier to bodily fluids, and may perform other functions (such as holding optical elements). An optical system 60, including, for example one or more optical elements, such as one or more lenses or composite lens assemblies, one or more suitable optical filters, or any other suitable optical elements, may aid in focusing reflected light onto the imager 46 and performing other light processing. Typically, the optical system 60 produces a circular image, but other image shapes may be produced. Instead of an imager sensing device, other sensing devices for sensing in-vivo data other than pressure, strain or stress may be used, such as pH sensors, etc.

In one embodiment, the imager 46 is a complementary metal oxide semiconductor (CMOS) image sensor. The imager 46 is typically an ultra low power imager and is provided in chip scale packaging (CSP). One suitable CMOS camera is, for example, a "camera on a chip" CMOS imager specified by Given Imaging Ltd. of Israel and designed by Photobit Corp. of California, USA, with integrated active pixel and post processing circuitry. Other types of CMOS imagers may be use. In another embodiment, another imager may be used, such as a CCD imager, or another image.

Illumination may be provided by LEDs or any other suitable illuminating element. According to one embodiment stress data or other data may be processed and translated by a processor (e.g., transmitter 41) to an output signal, such as, for example, a change in illumination intensity, frequency, or number of LEDs illuminated. Device 40 can thus provide a visible signal to indicate stress experienced by the device 40.

Figure 3:
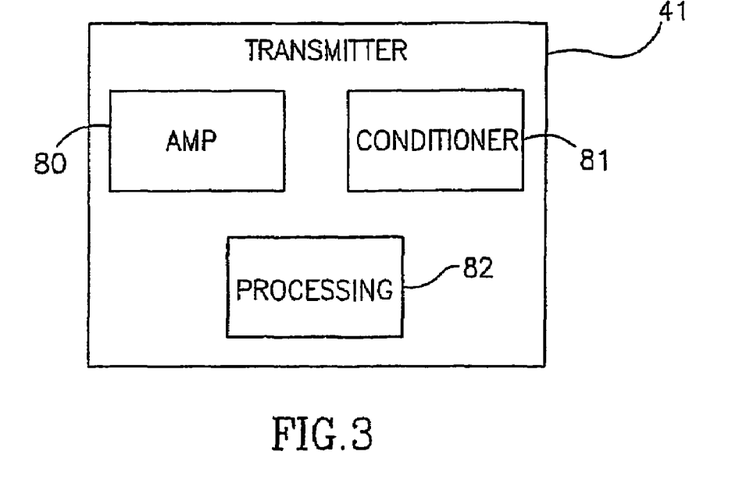
FIG. 3 is a block diagram of a transmitter according to one embodiment of the present invention.

Referring to FIG. 3, transmitter 41, typically an ASIC type circuit (although other types of circuits or processor may be used), may contain for example, an amplifier 80 for amplifying sin gauge 52 signals, a signal conditioner 81, for conditioning such signals, and/or processing circuitry 82 for processing such signals (amplifier 80, signal conditioner 81 and processing circuitry 82 are shown in FIG. 3A); portions or all of such functionality or circuitry may be located elsewhere within the device 40 or outside of the device 40. In one embodiment, transmitter 41 transmits strain or stress information to a receiver outside the patient's body, such as receiver 12 (FIG. 1). In one embodiment, the information from the strain gauge 52 is provided as an analog signal. Optionally the signal may be converted, for example, to an 8 bit digital signal, before being received by the transmitter, or may be produced as a digital signal. Transmitter 41 or another processing unit may process strain information before transmission; for example, the strain information may be converted to stress information. Varying rates of sampling may be used. For example, strain information may be sampled by the transmitter 41 and transmitted once every second; other rates may be used.

Depending on whether or not an imager or other sensor is included, the information obtained by device 40 may be, for example, a combination of endo-luminal pressure information and image data on the endo-luminal environment at the site correlating to the specific pressure data.

Figure 4:
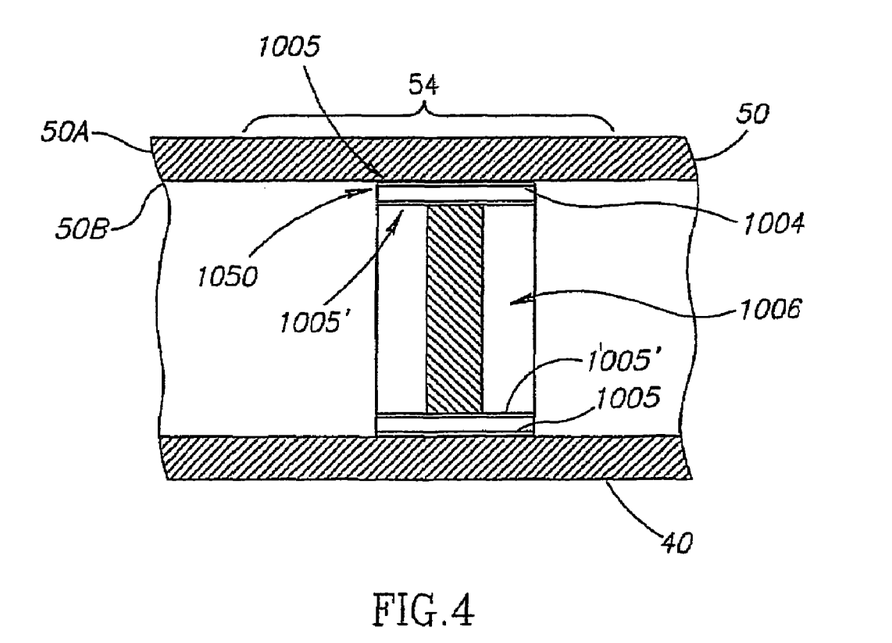
FIG. 4 depicts a portion of an in-vivo device according to one embodiment of the invention.

Another embodiment of the invention is schematically shown in FIG. 4, which depicts a portion of device 40, with an alternate embodiment of a stress or deflection sensor. The container or shell 50 has bonded to it on its inner layer 50*b* a shell deflection sensor 1050. Shell 50 may include a stress-responsive element or portion, such as portion 54. In the embodiment described in FIG. 4 the sensor 1050 is a capacitance shell deflection sensor, which includes an outer conducting ring 1005 and an inner conducting ring 1005'; however, other deflection sensors may be used. The sensor 1050 is connected by wires (not shown) to a power source and to a processor such as transmitter 41 that receives electrical signals from the sensor. When stress is applied to the shell 50, such as described above, the shell 50, which is stress-responsive at least in a portion (e.g., portion 54), deflects, causing the outer ring 1005 to be deflected towards the inner ring 1005'. Typically there is a rigid element 1006 which assists in immobilizing the inner ring 1005' such that deflection of the outer ring 1005 changes the spacing 1004 between the inner ring 1005' and outer ring 1005, thus proportionally changing the capacitance and thus the strength of the measured electric signal from the sensor. Proper calibration may be required for calculating the stress.

In other embodiments the sensor 1050 may be incorporated into or integrated within shell 50 rather than being bonded to the shell inner layer. According to this embodiment the shell outer layer 50a is stress-responsive and may deflect under stress, such as stress exerted by the GI tact walls and which may deflect the outer ring 1005 with it. The shell inner layer 50b may be a rigid element which assists in immobilizing the inner ring 1005' such that deflection of the outer ring 1005 changes the spacing 1004 between the inner ring 1005' and outer ring 1005, thus proportionally changing the capacitance and thus the strength of the measured electric signal from the sensor.

Figure 5A:
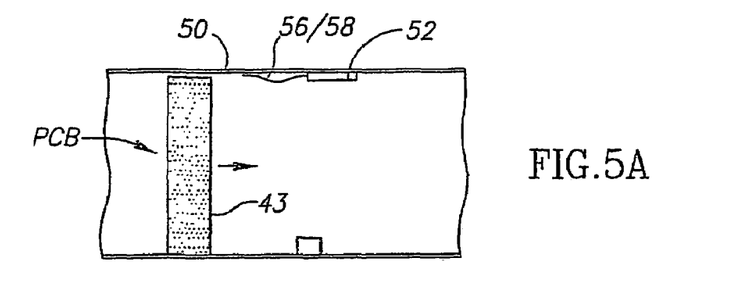
FIGS. 5A, 5B, 5C and 5D depict circuit boards in conjunction with strain gauges according embodiments of the present invention.
Figure 5B:
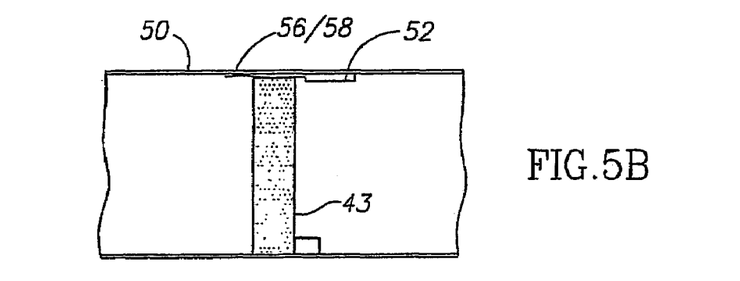

In one embodiment, a circuit board such as circuit board 43 is perpendicular to the axis of the device 40 and may be connected to, for example, strain gauge 52 or to sensor 1050 during manufacture. FIGS. 5A and 5B depict the assembly of the circuit board 43 and strain gauge 52 according to an embodiment of the present invention. While the description in FIGS. 5A and 5B is with reference to strain gauge 52, such an embodiment may be used with any suitable sensor, such as sensor 1050. Strain gauge 52 includes one or more wires, such as wires 56 and/or wire 58, which may be, for example spring contact type leads, which extend from the strain gauge 52 and compress between the circuit board 43 (or other components of the device 40) and the shell 50 when the circuit board 43 is moved towards the strain gauge 52 during manufacture. The circuit board 43 includes contact (not shown) wire contacting 58.

Figure 5C:
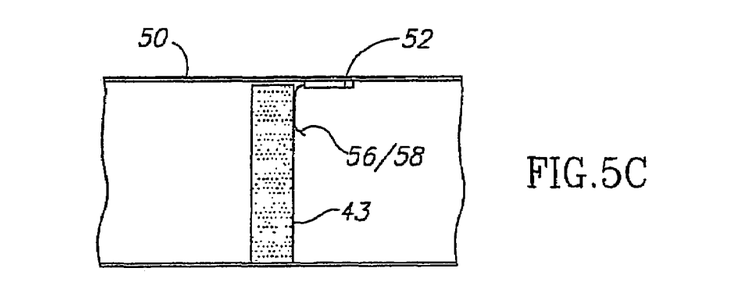

FIG. 5C depicts the assembly of the circuit board 43 and strain gauge 52 according to another embodiment of the present invention. One or more wire(s) 56 and 58 compress against the circuit board 43 when the circuit board is moved towards the strain gauge 52 during manufacture. In alternate embodiments, other methods of connecting the strain gauge 52 to other circuitry such as the circuit board 43 may be used; for example soldering.

Circuitry such as the transmitter 41 may be located other than on circuit board 43, circuit board 43 need not be in the position as shown, and a circuit board need not be used.

Figure 6:
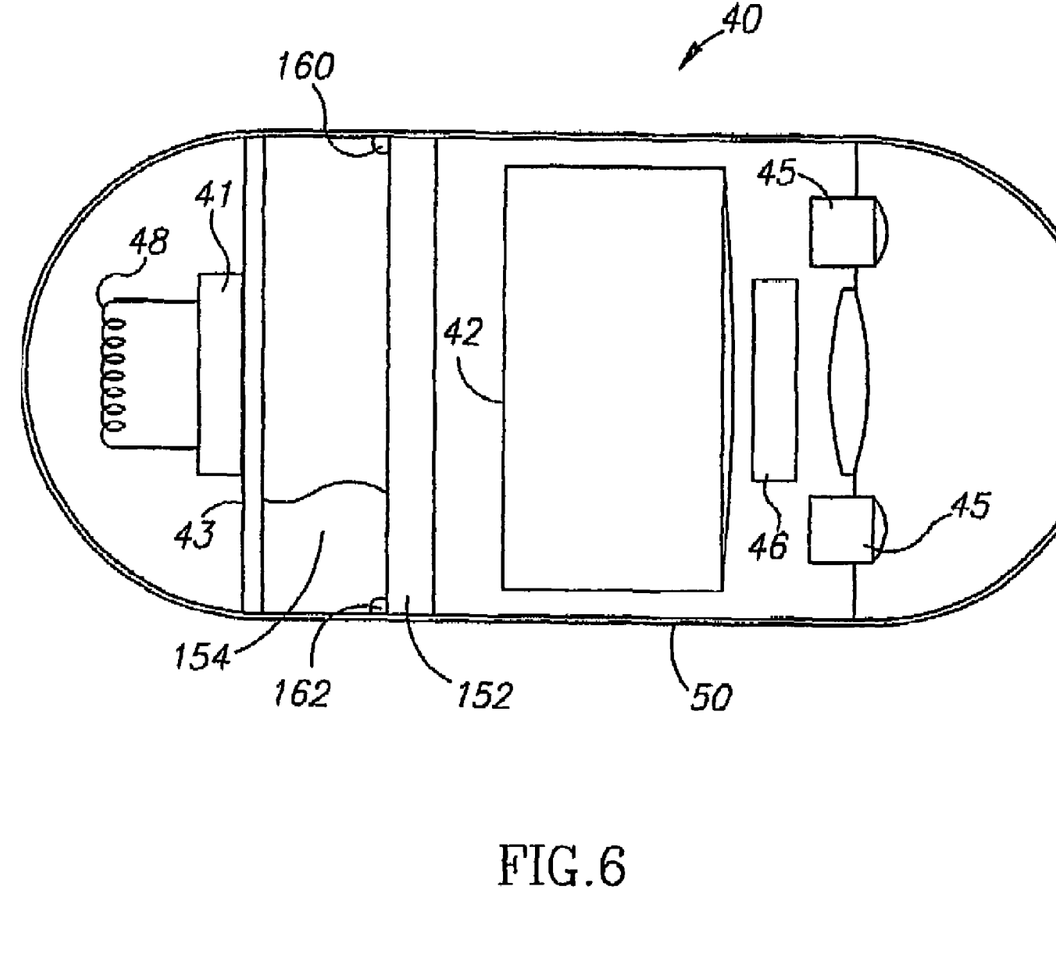
FIG. 6 depicts a schematic diagram of an in-vivo stress sensing device according to one embodiment of the present invention.

FIG. 6 depicts a schematic diagram of an in-vivo stress sensing device according to one embodiment of the present invention. Referring to FIG. 6, device 40 includes a shell 50, a strain gauge 152, an imager 46, one or more illumination sources 45, a power source 42, and a transmitter 41 which may transmit via an antenna 48. Strain gauge 152 is typically in the shape of a ring on the perimeter of the device 40 and, is closely associated with the shell 50. The shell 50 is substantially semi rigid, and may deform slightly under stress, typically stress exerted by the body lumen wall. Stress related deformation of shell 50 is conveyed to the closely associated strain gauge 152. For example, if the shell 50 is compressed by stress exerted by the GI tract wall, the strain gauge 152 is proportionally compressed. The strain gauge 152 typically includes a piezoelectric material such as PZT (piezoelectric zirconate titanates) or PVDF (Polyvinylidene Fluoride), or other suitable material, which, when compressed, emits an electric signal that is proportional to the amount of compression, or otherwise cares information on the amount of the compression. Wires 154 carry such electric pulses or signals to transmitter 41. Typically, strain gauge 152 is firmly attached to two walls of the shell 50, using, for example, epoxy attached to points 160 and 162 or other locations. Other attachment methods may be used. Alternately, strain gauge 152 may be attached to structures, which may carry deformation movement from the shell 50 to the strain gauge 152. In operation, when stress deforms the shell 50, the strain gauge 152 is compressed and emits electrical signals carrying information on the amount of the stress to the transmitter 41. As with other embodiments of the present invention, instead of an imager sensing device, other sensing devices for sensing in-vivo data other than pressure or stress may be used.

In one embodiment, the electrical pulses (e.g. electrical current) produced by piezoelectric material may be used to directly stimulate muscles in the area of passage for example, to enhance peristaltic motion in the small intestine.

Figure 5D:
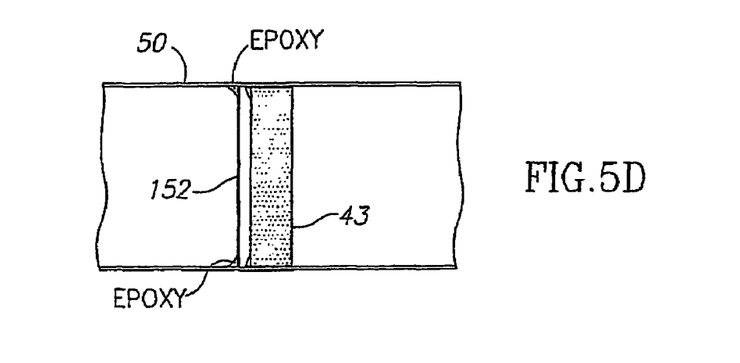

FIG. 5D depicts the assembly of a circuit board and strain gauge according to one embodiment of the present invention. The strain gauge 152 includes wires, springs or other electrical contacts (not shown), which contact the circuit board 43 when the circuit board 43 is moved towards the strain gauge 152 during manufacture. The circuit board 43 includes corresponding contacts (not shown). Other methods of assembly and configuration are possible.

Figure 7:
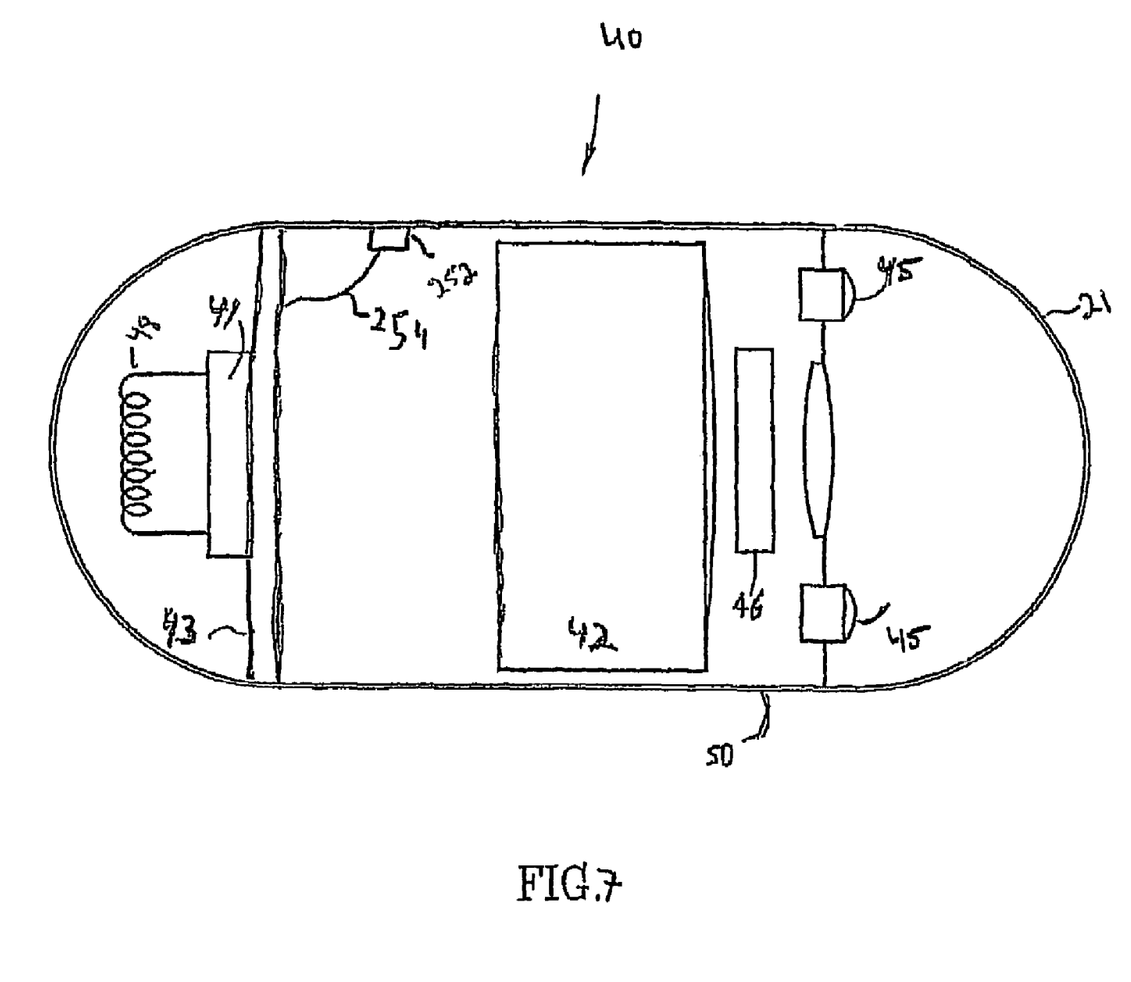
FIG. 7 depicts a schematic diagram of an in-vivo sensing device including a sensor such as an imager, according to one embodiment of the present invention.

FIG. 7 depicts a schematic diagram of an in-vivo pressure—sensing device according to one embodiment of the present invention, including another sensor such as an imager. Referring to FIG. 7, device 40 includes a shell 50, a pressure gauge 252, an imager 46, one or more illumination sources 45, (both typically situated behind optical window 21) a power source 42, and a transmitter 41 which may transmit via an antenna 48. Sensors other than imagers may be used. Pressure gauge 252 may be any known pressure gauge such as, for example, MOD. KSPH-4-2K-E4, provided by KYOWA, Japan, which may detect pressure and emit electric pulses or signals such as an analog voltage at mVolt level, indicating the amount of pressure, or otherwise carrying information on the amount of the pressure in the body lumen. One or more wires 254 carry such electric pulses or signals to the transmitter 41. Pressure gauge 252 may require power input. Typically, pressure gauge 252 extends to the space external to the device 40 via, for example, an opening in the shell 50, or may be otherwise exposed to external pressure. In operation, when the device 40 is under pressure, the strain gauge 252 detects such pressure and emits electrical signals carrying information on the amount of the pressure to the transmitter 41. Image data is collected by imager 46 and transmitted by the transmitter 41.

Processing and/or combining of pressure and image data may be performed. Such processing may be done on line, by an on processor within device 40, or post transmission, in, for example, an external receiver and/or display system, such as by processor 14 (FIG. 1). Online processing information may be stored for later inspection or may be transmitted. Online processing of stress or pressure information may, for example, allow the device 40 to make decisions according to stress or pressure; such decisions may be made externally and received by the device 40 as commands or other information. Shell 50 may or may not be compressible in such an embodiment.

Figure 8:
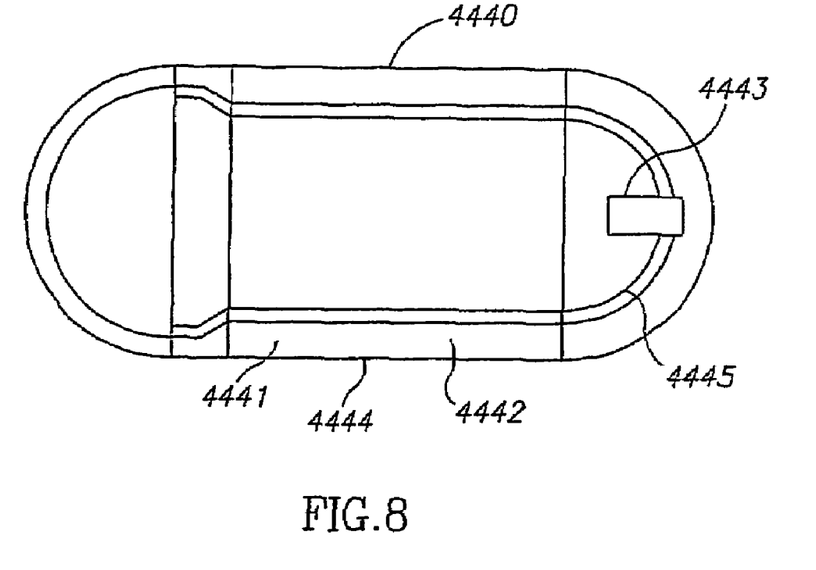
FIG. 8 is a schematic diagram of an in-vivo sensing device according to one embodiment of the present invention.

Reference is now made to FIG. 8 in which another embodiment of the invention is schematically illustrated. A device 4440 includes a space 4442 filled with fluid 4441. In connection with space 4442 is a pressure gauge 4443. According to one embodiment the outer shell 4444 of the fluid filled space, or a portion thereof, which faces the body lumen, and is made of a pliant material, such as a suitable rubber or plastic. Space 4442 includes an inner wall or shell 4445. The pressure gauge 4443 is typically immersed in or in contact with the fluid 4441. Typically, pressure or stress exerted on a point on the pliant shell 4444 is transmitted into the fluid filled space 4442 as hydrostatic pressure and is sensed by the pressure gauge 4443. The pressure gauge 4443 may be connected to any of the outer or inner shells 4444 or 4445 of the space 4442, to another structure, or it may be free to float within the space 4442. Device 4440 may include other components s o to those described in other in-vivo devices herein, such as a transmitter, power source, imaging system, etc., and may transmit stress, strain, pressure, or other data to an external receiving and display system, such as that described with respect to FIG. 1.

According to one embodiment the space 4442 forms a sleeve on the inside perimeter of the device 4440, around all or part of the device 4440. According to another embodiment the space 4442 may include parts of or the whole inner space of the device 4440. Stress or pressure exerted on a relatively large area of the device 4440 may thus be sensed.

Typically, the fluid 4441 is a liquid. According to one embodiment the fluid 4441 is a dielectric liquid, such as glycerin, such that various electronic parts of the device 440 may be immersed in the fluid 4441 with no impairment to operation. According to one embodiment the device 4440 includes other sensing systems, such as an optical dome and imaging system, for example, as described herein. The configuration of the device 4440 and space 4442 may differ from that illustrated.

In one embodiment, information on, for example, pressure, strain or stress may be communicated from a device via an imaging system. Embodiments of a device, system and method for transmitting non-image data via, for example, an imaging system are described in U.S. Patent Application 60/429,562 filed 29 Nov. 2002 and entitled "Method, Apparatus and System for Transmitting Non-Image Data in an In Vivo Imaging System", assigned to the assignee of the present invention and incorporated by reference in its entirety. However, other methods and systems for transmitting information via an imaging system may be used in accordance with embodiments of the present invention.

Figure 9:
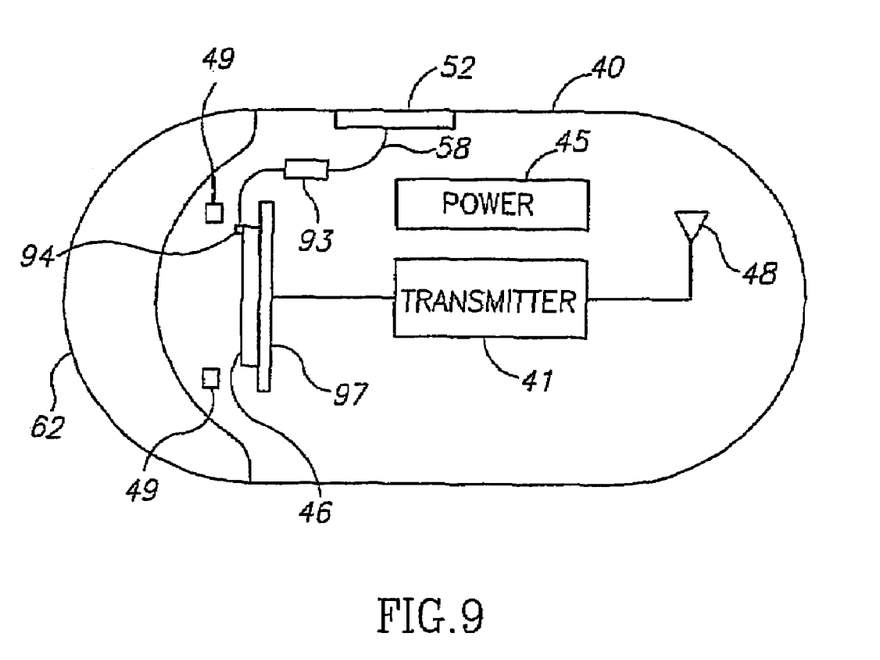
FIG. 9 depicts an in-vivo device where non-image data may be transmitted via an imaging system, according to an embodiment of the invention.

FIG. 9 depicts an embodiment of The invention where non-image data-may be transmitted via an imaging system. Referring to FIG. 9, device 40 may include an imager 46, an optical system (not shown), a dome 62, a illumination device driver circuit 93, an illumination device 94 (typically separate from an illumination device used to illuminate an area for viewing, such as illumination elements 49, although the same illumination system may be used), and a processing chip or circuit 97 for, for example, processing the signals generated by an imager 46. All or part of the functionality of illumination device driver circuit 93 and circuit 97 may be performed by the transmitter 41, the imager 46, or by a processor separate from device 40. Device 40 may include components and functionality similar to the in-vivo devices described elsewhere herein.

Typically, the imager is rectangular in shape, more typically square (e.g., a 256×256 CMOS array), but may of course have other shapes and dimensions. The image produced by the optical system is typically substantially circular in shape. Other image shapes may be produced, such as irregular shapes, ovals, etc. Where the image produced by the optical system does not entirely fill the typically rectangular imager 46, there are areas of the imager 46 (e.g., corner 63 in FIG. 10) that are not used to receive image information. Non-image information (e.g., pressure information, stress information, etc.) is conveyed using one or more of these areas otherwise unused to capture image information.

In alternate embodiments, other imager shapes or configurations may be used. It should be emphasized that although non-used image areas are discussed, some of the image pixels may be "sacrificed" in favor of additional data.

The in vivo device 40 measures or observes the non-image data using a sensor such as strain gauge 52 or another shad or pressure sensor. The sensor may be of another configuration or located differently from strain gauge 52. A signal from the strain gauge 52 which is expressed as an electrical quantity, such as voltage, may be propagated on wire 58. For example a mare pressure sensor (e.g. by Endveco, model 8507C) may measure pressure in range of 2 to 50 pounds per square inch, with the full range output of 300 mv. The output from the strain gauge 52 or other sensor can also be a signal, frequency, bit pattern, pulse repetition, pulse width, etc.

This electrical signal or quantity produced by the strain gauge 52 is relayed to an illumination device 94 (such as, for example, a "white" or monochromatic LED, although other types of illumination devices may be used) such that the variation in voltage produces a variation in optical output (e.g., color or brightness) of the illumination device 94. The electrical signal or quantity may be relayed to the illumination device 94 directly or indirectly through, for example, an optional illumination device driver circuit 93. The illumination device driver circuit 93 may be a separate unit or set of components or, for example incorporated into the processor 97 or transmitter 41 or other component. The output of the sensor may modulate the illumination device 94 in different manners, including, but not limited to: light intensity modulation, light frequency (e.g., color) modulation, light pulses repetition modulation, light pulses width modulation, etc. The light from illumination device 94 is recorded by the imager 46 and transmitted by the transmitter 41.

Figure 11:
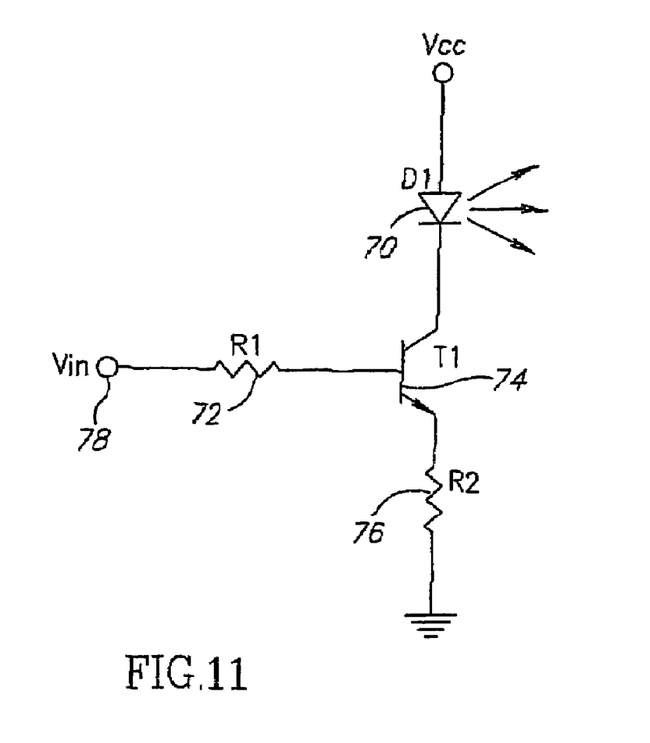
FIG. 11 is an example of a driver circuit that may be used in connection with the in-vivo device of FIG. 9, according to an embodiment of the present invention.

FIG. 11 is an example of an illumination device driver circuit that may be used in connection with an embodiment of the present invention. Illumination device 94 provides illumination proportional to the driving voltage at terminal 78. The driver is based on the transistor amplifier 74 with two resistors 72 and 76, whose characteristics determine the working point.

Figure 10:
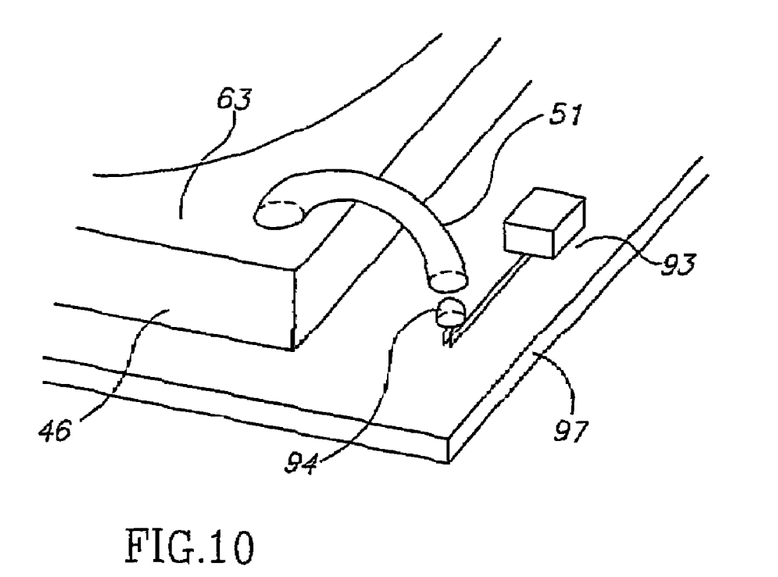
FIG. 10 depicts a portion of the in-vivo device of FIG. 9, according to an embodiment to the invention.

Referring to FIG. 10, the illumination from the illumination device 94 may be relayed via, for example, an optical guide 51 (e.g., an optical fiber, plastic conduit, prism, etc.) to a typically unused area of the imager 46 (e.g., a corner, although other areas may be used). The illumination device 94 and/or any optical equipment (e.g., optical guide 51) associated with the optical element may be covered or associated with shielding (e.g., a baffle, a coating, not shown) to prevent interference with the image data being sensed at the imager or with light provided by other illumination devices. The shape or other design of optical components, such as the dome 62, may eliminate the need for shielding by, for example, directing excess light from the illumination device 94 away from the imager 46.

In alternate embodiments, "used" areas—that is, areas receiving image information—may be used to receive input from the illumination device. Other methods of conveying light from the illumination device 94 may be used. For example, no light guide need be used, and/or the illumination device 94 may be mounted directly on the imager 46.

Illumination which varies with the non-image information read by, for example, stain gauge 52 is received at the imager 46, possibly processed, and transmitted and received in a manner similar to image information. At an external receiver or processor such as the receiver 12 (FIG. 1), the optical non-image data may be, for example, processed or interpreted, and may be displayed accordingly. An external display or processor system such as data processor 14 may process and translate the non-image data, e.g. pressure or strain data, into the originally sensed data (e.g., temperature) or cause it to be displayed it as image data.

Referring to FIG. 1, data processor 14 operates software (not shown), which, in conjunction with basic operating software such as an operating system and device drivers, controls the operation of data processor 14. Typically, the software controlling data processor 14 includes code written in the C++ language, but may be implemented in a variety of known methods. Data processor 14 may include graphics software or hardware.

The data collected and stored may be stored indefinitely, transferred to other locations, or manipulated or analyzed. A health professional may, for example, use the data to diagnose pathological conditions of the GI tract, for example, by comparing stress data obtained from a subject with stress data obtained from a normal or healthy subject, and, in addition, the system may provide information about the location of these pathologies. While, using a system where the data processor storage unit 19 fist collects data and then transfers data to the data processor 14, the data is not viewed in real time, other configurations allow for real time viewing.

While, typically, information gathering, storage and processing are performed by certain units, the system and method of the present invention may be practiced with alternate configurations. The device 40 may have other shapes, and have shells with other deformable regions; in alternate embodiments, deformable regions need not be used. The components gathering data need not be contained in a capsule, but may be contained in any other vehicle suitable for traversing a lumen in a human body, such as an endoscope, stent, catheter, needle etc. Furthermore while typically the components accepting processing and displaying the data are contained within a world on system or PC, other systems may be used, and other (e.g. distributed) components may perform data receiving processing and displaying.

Figure 12:
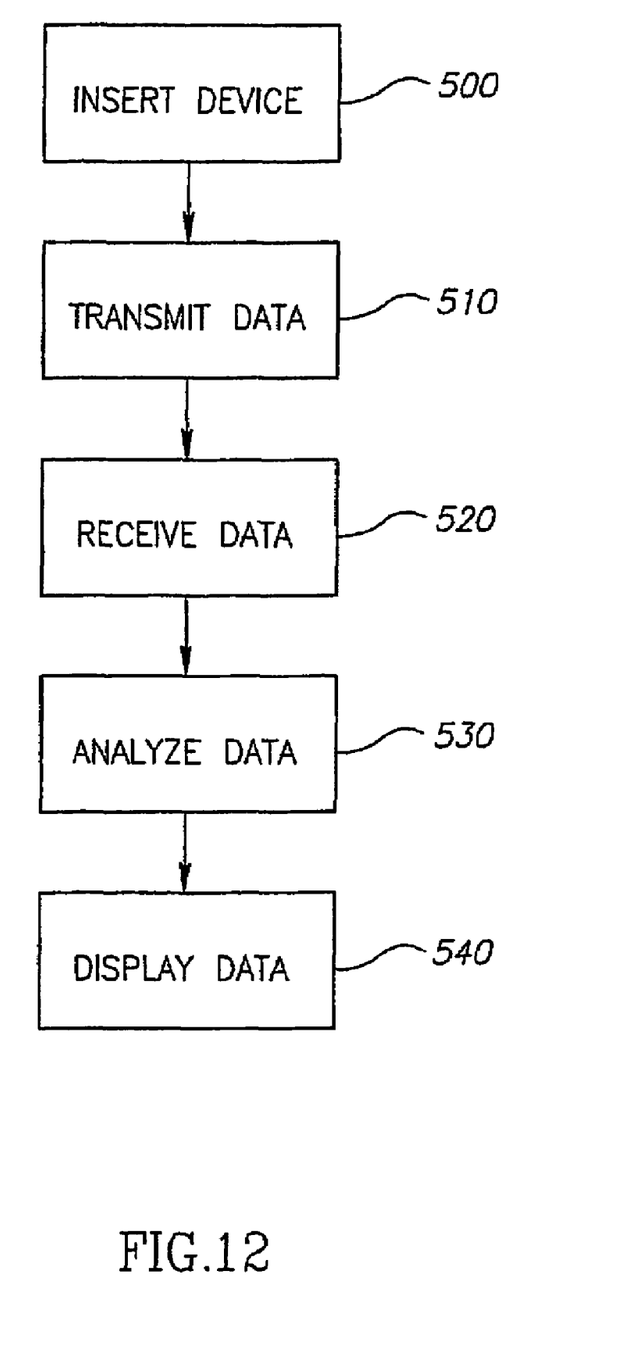
FIG. 12 depicts a method according to one embodiment of the present invention.

FIG. 12 depicts a method according to one embodiment of the present invention. Referring to FIG. 12, in operation 500, an in-vivo device is inserted into a body. For example, the device may be ingested.

In operation 510, the in-vivo device transmits stress or pressure data. Data in addition to such data may also be transmitted.

In operation 520, the stress or pressure data is received by a processing system For example the data may be received by a receiving system, which may be separate from, within or connected to a workstation, and then may be transmitted or sent from the receiving system and received at the processing system.

In operation 530, the processing system analyzes the stress or pressure data. For example, based on patterns of stress or pressure, it may be determined that the in-vivo device is in or has moved from one portion of a body lumen to another, that an in-vivo condition exists, etc.

In operation 540, the processing system may display the analyzed data.

Other steps and series of steps may be used.

It will be appreciated by persons skilled in the art that the present invention is not limited by what has been particularly shown and described herein above. Rather the scope of the invention is defined by the claims, which follow.

We claim:

1. A system for collecting and displaying in vivo data, the system comprising:
   a swallowable in vivo imaging device for collecting in vivo images and in vivo pressure data, wherein said in vivo device, when swallowed within a patient's lumen, has no physical connection to outside of said patient's body, said device comprising:
      a housing including an optical dome, a shell enclosing components of said device, and a pliant sleeve surrounding said shell, said pliant sleeve defining a space outside the shell and inside the pliant sleeve, said space being filled with a fluid,
      an imaging system enclosed in said shell behind said optical dome, and
      a pressure gauge in contact with the fluid in said space between the shell and the pliant sleeve; and
   a display to display in vivo pressure data provided by said device simultaneously with correlating in-vivo images provided by the device, wherein said pressure data displayed is measured at a correlating site of the image displayed simultaneously.

2. The system of claim 1 comprising an illumination unit to produce illumination in proportion to a signal from the pressure gauge.

3. The system of claim 1, further comprising:
   a receiving unit to receive pressure data from an in-vivo device; and
   a controller to analyze the pressure data and to determine a location of the in-vivo device based on said pressure data.

4. The system of claim 1 further comprising a transmitter to transmit in vivo pressure data.

5. The system according to claim 1 wherein said pressure gauge is attached to said shell.

6. The system according to claim 1 wherein said pressure gauge is attached to said pliant sleeve.

7. The system according to claim 1 wherein the imaging system comprises an imager, illumination elements to illuminate an in vivo area and an optical element to focus reflected light onto the imager.

8. The system according to claim 7 wherein the optical dome is a barrier to body fluids.

9. The system according to claim 1 wherein the fluid is a liquid.

10. The system according to claim 9 wherein said liquid is dielectric liquid.

11. The system according to claim 10 wherein said pressure gauge is immersed in said dielectric liquid.

12. The system according to claim 10 wherein at least one element of said device is immersed in said dielectric liquid.

* * * * *